United States Patent [19]

Samuels

[11] Patent Number: 5,843,108
[45] Date of Patent: Dec. 1, 1998

[54] OVER THE WIRE SCAPEL

[76] Inventor: Shaun Laurence Wilkie Samuels, 1055 Sonoma Ave., Menlo Park, Calif. 94025

[21] Appl. No.: 956,955

[22] Filed: Oct. 23, 1997

[51] Int. Cl.$^6$ .................................................... A61B 17/32
[52] U.S. Cl. ........................ 606/167; 606/167; 606/190; 606/185; 604/164; 604/168; 604/247
[58] Field of Search .................................. 606/167, 190, 606/185; 604/164, 168, 247

[56] References Cited

U.S. PATENT DOCUMENTS

| | | | |
|---|---|---|---|
| 4,468,224 | 8/1984 | Enzmann | 604/247 |
| 4,633,860 | 1/1987 | Korth et al. . | |
| 4,955,890 | 9/1990 | Yamamoto et al. . | |
| 5,026,384 | 6/1991 | Farr et al. . | |
| 5,242,410 | 9/1993 | Melker | 604/164 |
| 5,295,969 | 3/1994 | Fischell et al. | 604/168 |

*Primary Examiner*—Michael Powell Buiz
*Assistant Examiner*—Vy Q. Bui
*Attorney, Agent, or Firm*—Rudnick & Wolfe; William T. Rifkin, Esq.; R. Blake Johnston, Esq.

[57] ABSTRACT

An over the wire scalpel for performing a dermatotomy that produces a skin nick features a triangular shaped blade with a pair of cutting edges that meet to define a tip. The blade is connected to a handle and a central lumen passes through both. The leading opening of the lumen is positioned at the blade tip so that it is symmetrically abutted by the cutting edges. A blocker that limits the depth of blade travel is positioned upon the handle adjacent to the blade. A stylus may be placed within the central lumen so that the scalpel may be used without a guidewire or with a guidewire that has a diameter significantly smaller than that of the central lumen.

5 Claims, 3 Drawing Sheets

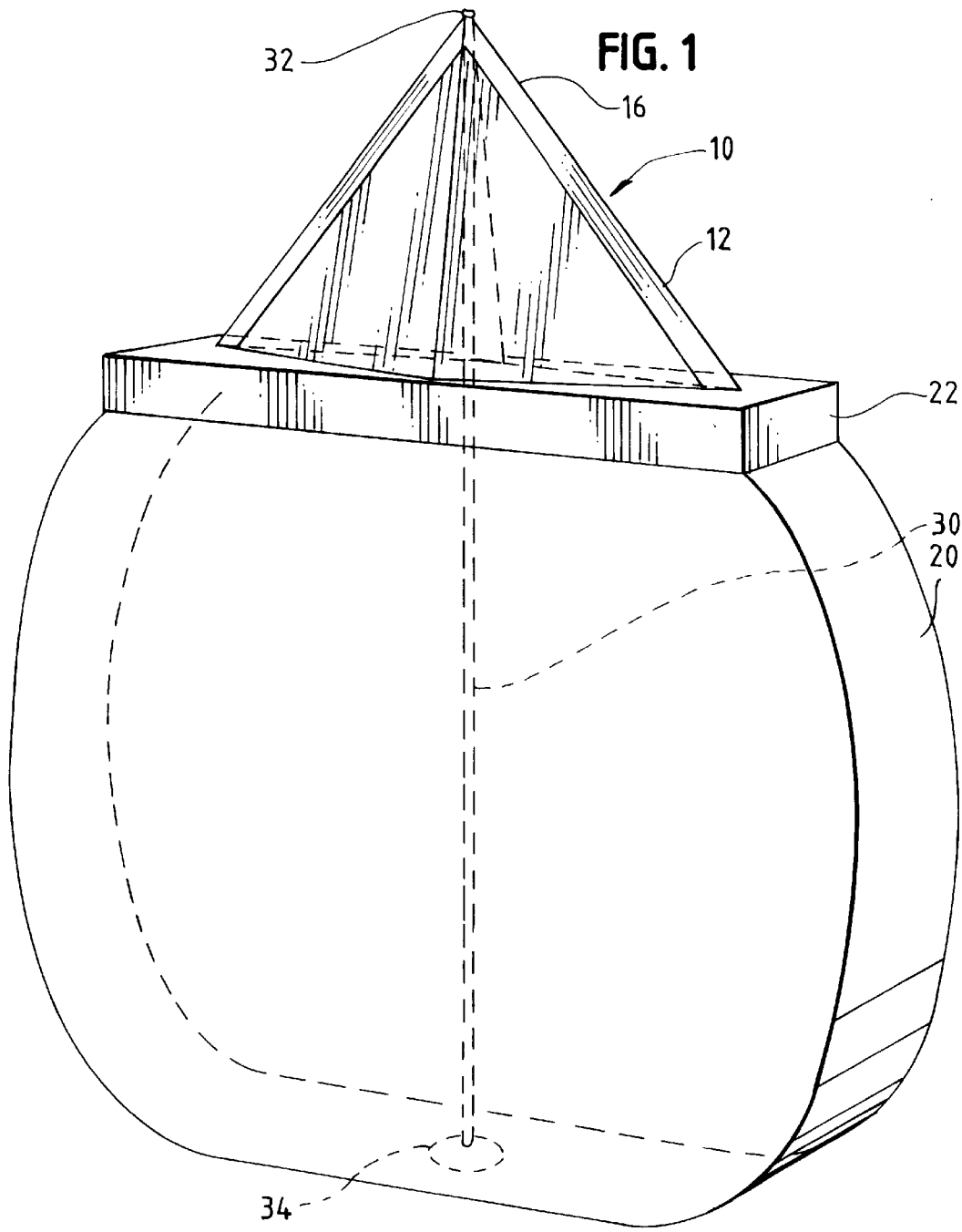
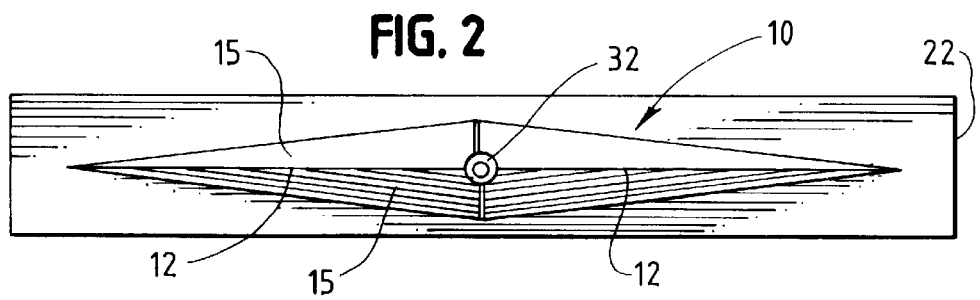

OVER THE WIRE SCAPEL

BACKGROUND

Recently, interventional radiologic techniques have been developed whereby procedures that previously required surgical intervention are instead performed percutaneously. With interventional radiology, tubular structures in the human body, such as the drainage system of the kidneys, the bile ducts and the vascular system, are accessed and navigated by a wire that is steerable by the doctor. The wire passes from outside of the patient's body, through his or her skin, that is, percutaneously, and then into the internal tubular structure of interest. Once the wire is positioned in the desired location, medical devices, such as catheters, may be passed over the wire and thereby guided into the tubular structure so that the desired medical procedure may be performed.

To install the wire, a hollow needle is initially placed through the patient's skin and into the tubular structure of concern. The wire is then passed through the lumen of the needle and into position within tubular structure. The needle is then withdrawn. At this point in the procedure, it becomes necessary to pass over this guidewire catheters or other devices which allow investigation or treatment of the tubular structure. Such devices by necessity are larger than the guidewire over which they are passed and hence cannot pass through the skin via the small hole made by the initial needle puncture. For this reason, a dermatotomy is performed during which a small skin incision, also known as a "skin nick", is made adjacent to the point of entry of the guidewire into the skin.

Skin nicks have traditionally been created using standard surgical scalpels. These scalpels are disposable and feature triangular blades that are attached to polymer plastic handles. The physician uses such a scalpel to made the small incision as close as possible to the wire and its point of puncture.

The disadvantages of this procedure arise from the difficulties encountered in creating a skin nick of an appropriate size and depth which is centered on the entry point of the wire. Oftentimes, after the wire has been placed, there is a small amount of bleeding from the puncture site which obscures the precise point of entry of the guidewire. As a result, it is difficult for the physician to direct the standard scalpel blade to a position directly adjacent to the wire. Frequently, during such attempts, a small skin bridge remains between the guidewire and the skin nick. This skin bridge restricts the passage of larger devices over the wire and through the skin. If the physician attempts to force the device past the skin bridge, it will tear and bleeding will be increased. In such a situation the scalpel must be used again in an attempt to remove the skin bridge. This is time consuming and difficult.

A further disadvantage of the procedure is that the current design of the scalpels does not limit the depth or length of the skin nick. This can be of great concern when the tubular structure in question is close to the skin surface. In this circumstance, an inadvertantly deep skin nick may sever the structure of concern with potentially disastrous consequences.

Still another disadvantage of the procedure is that during the formation of the skin nick with the wire in place, it is possible to damage or sever the guidewire. The latter would require removing the wire and starting the procedure again. A severed wire could also become lost in the subcutaneous tissue and be very difficult to retrieve. If the wire were damaged, but not severed, it would be difficult to pass a device over the damaged portion.

In response to the above difficulties, over the wire incision devices have been developed. U.S. Pat. No. 4,633,860 to Korth et al. discloses a device for forming a canal in the body of a patient through the skin and subcutaneous tissue to the kidney so that an endoscopic instrument may be inserted. The device features a pair of blades symmetrically mounted upon a tube through which a guidewire passes. While this device works for its intended purpose, the creation of a canal in the human body, its blade design is not well suited for use in creating skin nicks. More specifically, the blades of Korth et al. are arcuate shaped to allow complete insertion and withdrawal in different planes so as to create a canal. As such, it would be difficult to partially insert the blades of Korth et al. to create a shallow skin nick. Furthermore, it is desirable that the skin nick be deepest at the location of the wire and then gradually become shallower as the radial distance from the wire increases (ie: V-shaped). This allows a device such as a catheter, as it is guided along the wire, to smoothly pass into and through the skin. The arcuate shape of the blades of Korth et al. make the achievement of such an incision difficult.

U.S. Pat. No. 4,955,890 to Yamamoto et al. discloses a surgical skin incision device that features a tube with a pair of blades mounted symmetrically thereon. This structure, which is shared with Korth et al., causes the Yamamoto et al. and Korth et al. devices to have a number of disadvantages. One such disadvantage is that the tube causes the device surface initially contacting the skin to be blunt rather than sharp. While this provides the benefit of dilated skin at the cutting site, thus resulting in a cleaner cut near the edges of the incision, it also causes the cutting function to be compromised near the wire.

The manufacture of the Korth et al. and Yamamoto et al. devices require that cutting blades be individually attached to a tube. This is an intricate, and thus labor intensive and costly, procedure. Furthermore, the devices of Korth et al. and Yamamoto feature handles that are attached to their tubes. Such a configuration increases manufacturing costs even further. In addition, the handles disclosed by Korth et al. and Yamamato et al. are significantly larger than their blade portions. This decreases the ease at which the devices may be handled during intricate procedures.

Accordingly, it is an object of the present invention to provide an over the wire scalpel that makes it easier to create shallow, V-shaped incisions.

It is also an object of the present invention to provide an over the wire scalpel that dilates the skin at the cutting site without compromising cutting performance near the wire.

It is a further object of the present invention to provide an over the wire scalpel that may be easily and inexpensively manufactured.

It is a further object of the present invention to provide an over the wire scalpel that is easily manipulated for intricate cuts.

It is a further object of the present invention to provide an over the wire scalpel that may be used to create skin nicks without a guidewire.

It is a further object of the present invention to provide an over the wire scalpel whereby a single scalpel may be used with a variety of guidewire diameters.

SUMMARY

The present invention is directed to an over the wire scalpel for performing a dermatotomy whereby a skin nick is made. The over the wire scalpel features a blade having a pair of cutting edges that define a V-shape. A handle that a physician may easily hold between his or her fingers is connected to the blade. A blocker or stop is positioned upon the handle and adjacent to the blade so as to restrict travel of the blade into the patient's skin. The blade and handle have a central lumen passing therethrough that receives a guidewire. The central lumen has a leading opening through the tip of the blade.

The blade, in cross section, is generally diamond shaped (see FIG. 2). The thickest portion of the blade is adjacent the central lumen. The blade tapers so as to ultimately define the pair of cutting edges. Such a blade shape allows the scalpel to dilate the skin so as to improve cutting without degrading cutting performance in the region of the central lumen.

A stylus with a pointed end may be placed within the central lumen of the scalpel to allow its use without a guidewire. Alternatively, the stylus may itself include a lumen that allows the scalpel to be used with a guidewire that has a diameter that is significantly smaller than that of the central lumen.

For a more complete understanding of the nature and scope of the invention, reference may now be had to the following detailed description of embodiments thereof taken in conjunction with the appended claims and accompanying drawings.

BRIEF DESCRIPTION OF THE DRAWINGS

FIG. 1 shows a side elevation view of an embodiment of the over the wire scalpel of the present invention;

FIG. 2 shows an end view down the axis of the blade towards the handle of the over the wire scalpel of FIG. 1;

DESCRIPTION

Figure 3A:
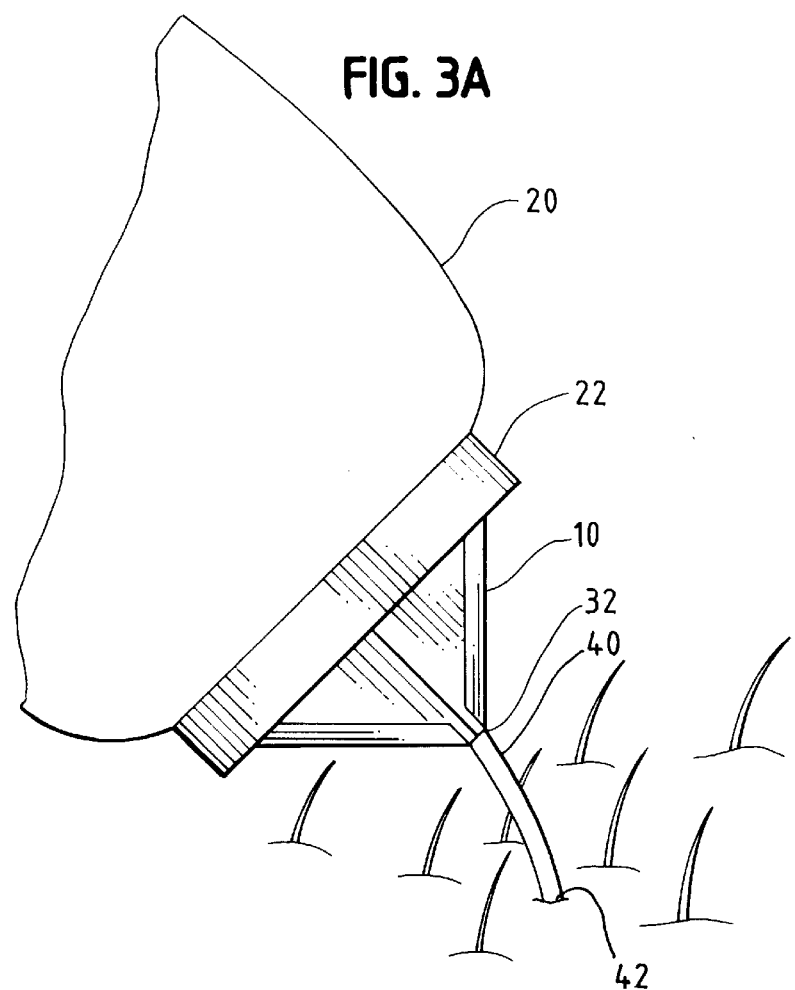
FIGS. 3A and 3B show the over the wire scalpel of FIG. 1 being passed over a guidewire to create a skin nick.

Referring to FIG. 1, an embodiment of the over the wire scalpel of the present invention is shown. This scalpel allows a dermatotomy to be performed during which a skin nick is created that extends from, and abuts, the entry site of a previously placed guidewire.

As shown in FIG. 1, the scalpel features a blade, indicated generally at 10, with a pair of cutting edges 12 and a pair of opposing triangular blade sides, one of which is indicated at 15. Cutting edges 12 meet to form the tip 16 of the blade 10. The blade 10 is preferably constructed of metal typically used for surgical scalpel blades, that is, surgical grade stainless steel. However, other suitable metals, or even biocompatible polymer plastics, could be used for its construction.

Attached to the blade 10 is handle 20. Handle 20 is shaped so that it may be easily held between the fingers of the physician. By restricting the size of handle 20 near blade 10, the scalpel may be easily manipulated by the physician so that intricate incisions may be made with great accuracy. Handle 20 is preferably composed of plastic polymer and may be joined to blade 10 by an adhesive or corresponding notch formations within the two pieces. Alternatively, blade 10 and handle 20 may be formed as an integral piece of the same material. This could reduce manufacturing costs.

Positioned between blade 10 and handle 20 is blocker 22. As may be seen in FIG. 1, blocker 22 has a width greater than that of the blade 10. As will be discussed below, this is necessary so that the depth of blade travel into the patient's skin is limited. Blocker 22 may be formed integral with blade 10, handle 20 or both.

Extending through blade 10, handle 20 and blocker 22 is a central lumen, shown in phantom at 30 in FIG. 1. As may be seen in FIG. 1, central lumen 30 has a leading opening 32 at blade tip 16. A central lumen trailing opening 34 is formed in handle 20. Central lumen 30 is sized so that it may receive a guidewire thus permitting the scalpel to slide along the guidewire to the patient's skin. Blade 10 is preferably symmetrical about the central lumen opening 32 so that symmetrical skin nicks may be produced. A scalpel may optionally include a number of blades symmetrically mounted about a common central lumen so that a spoke-wheel type incision may be created. This may be particularly desirable when larger devices must be passed over the guidewire and into the patient.

FIG. 2 shows an end on view of the blade 10 looking into the leading opening 32 of the central lumen 30. As may be seen by FIG. 2, blade configuration is preferably diamond shaped in cross section with the thickest portion of the diamond surrounding leading opening 32 (and thus central lumen 30). The cross section of blade 10 tapers down from its diamond shape to ultimately define cutting edges 12. As a result, the portion of the blade surrounding the central lumen has a greater average thickness than other portions of the blade. This allows the blade to slightly dilate, or pull apart, the skin as it makes its incision. This facilitates creation of the skin nick and results in a sharper, better defined (ie: "cleaner") cut. Because the cutting edges symmetrically abut leading opening 32, and the blade thickness gradually decreases as the distance from it increases, the scalpel of the present invention provides skin dilation without compromising cutting in the vicinity of the guidewire entry site.

Figure 3B:
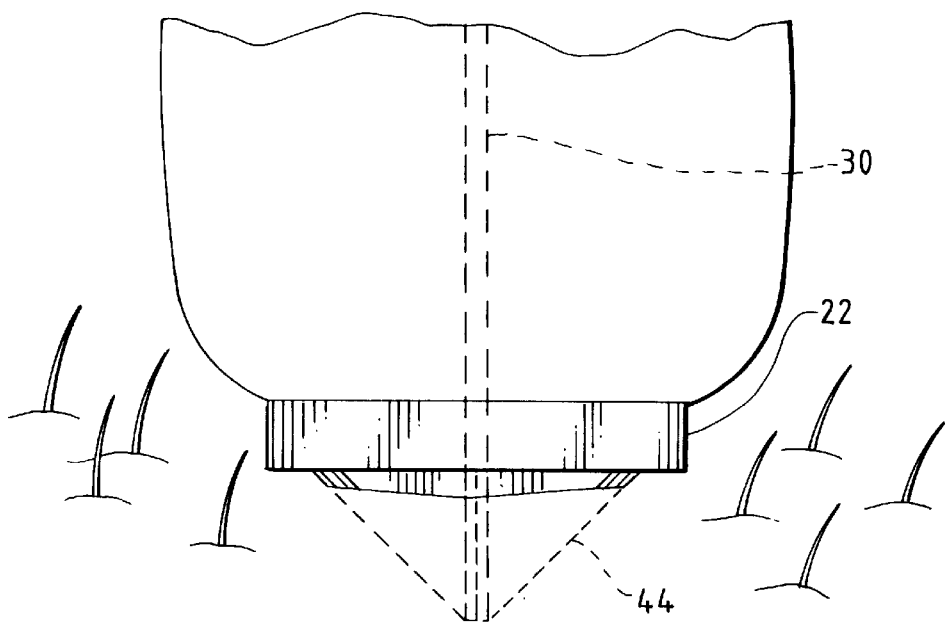

Turning to FIGS. 3A and 3B, a method of using the over the wire scalpel of the present invention to perform a dermatotomy is illustrated. As shown in FIG. 3A, a guidewire 40 enters the patient's skin at site 42, having been previously inserted using an initial puncture needle as is well known in the art. Guidewire 40 is received in leading opening 32 so that it passes through the central lumen 30 (FIG. 3B) of the over the wire scalpel. Leading opening 32 and central lumen 30 are only very slightly larger than guidewire 40 so that, while the over the wire scalpel may slide along guidewire 40, minimal space is present between guidewire 40 and the leading opening 32.

The physician slides the scalpel along guidewire 40, via handle 20, until the tip of blade 10 comes into contact with the patient's skin. As illustrated in FIG. 3B, blade 10 is then advanced into the patient's skin until blocker 22 impedes further travel. As such, blocker 22 limits the depth of the skin nick 44 thereby formed. As shown in phantom, skin nick 44 is deepest at the location of the wire and then is gradually shallower as the distance from the wire increases. This allows a device such as a catheter, as it is guided along the wire, to smoothly pass into the skin. Once skin nick 44 is created, the dermatotomy is complete. The scalpel is then withdrawn from the skin and slid off of the free end of guidewire 40.

Figure 4A:
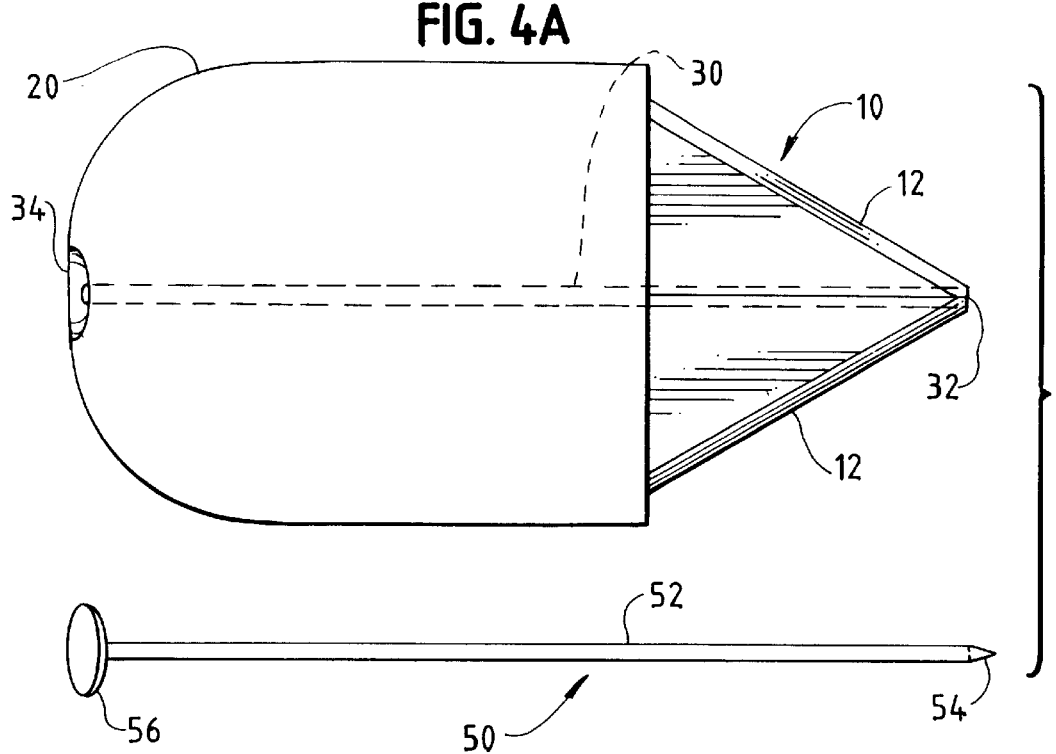
FIGS. 4A and 4B show a stylus before (FIG. 4A) and after (FIG. 4B) insertion into the central lumen of the over the wire scalpel of the present invention.
Figure 4B:
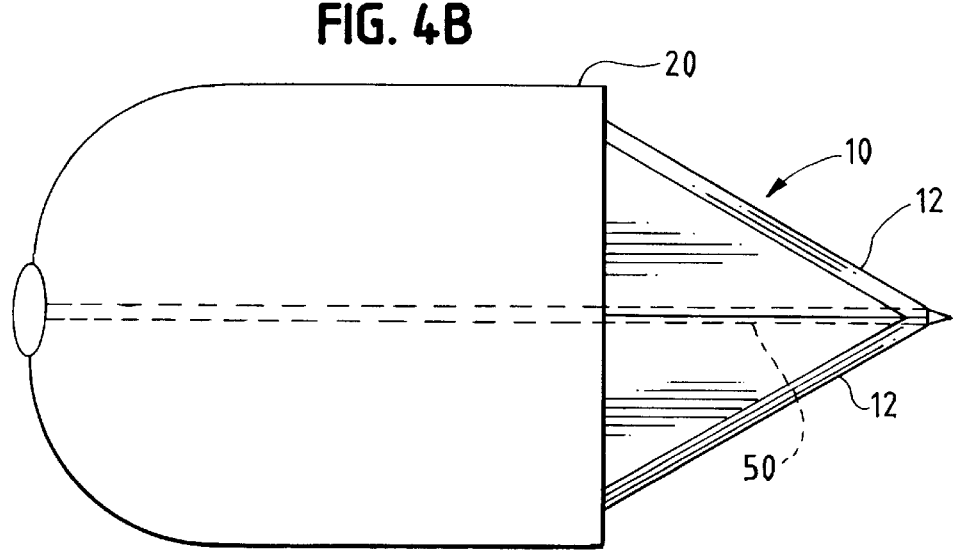

As shown in FIGS. 4A and 4B, a stylus, indicated generally at 50, may be inserted into the central lumen 30 of the scalpel so that it may be used to create skin nicks without the use of a guidewire. Stylus 50 features a stem 52 that is preferably composed of the same metal as blade 10. One end of the stem 52 is sharpened so as to form pointed end 54 while the other end is connected to base 56. While the entire stylus 50 may be formed out of a single piece of material, base 56 is preferably made of plastic polymer and attached to stem 52 with adhesive or the like to make handling easier.

As shown in FIG. 4B, stem 52 is placed through central lumen 30 by introducing pointed end 54 into trailing opening 34. The entire length of stem 52 is passed through central lumen 30 until its travel is halted by the engagement of base 56 with trailing opening 34. Base 56 and trailing opening 34 are sized so that they snap together so that stylus 50 doesn't fall out of the scalpel as it is being handled. Pointed end 54 is shaped so that it conforms with cutting edges 12 when stylus 50 is positioned within the scalpel. As a result, in this configuration, blade 10 features a continuous sharp surface.

Figure 5:
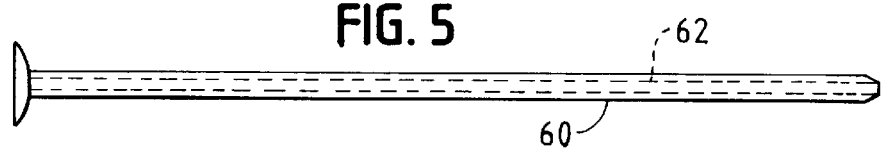
FIG. 5 shows an alternative embodiment of a stylus that may be inserted into the central lumen of the over the wire scalpel of the present invention.

An alternative embodiment of the stylus is shown in FIG. 5 at 60. Stylus 60 is identical to stylus 50 except that it features a lumen, indicated in phantom at 62, through its longitudinal axis. Stylus lumen 62 is sized so that it can accommodate a guidewire that has a diameter that is significantly smaller than that of central lumen 30 (FIG. 4A). As a result, when stylus 60 is placed within central lumen 30, the scalpel may be used with a smaller diameter guidewire. Furthermore, a physician with access to a number of styluses, with varying lumen diameters, can use a single scalpel with a variety of guidewire diameters.

While preferred embodiments of the invention have been shown and described, it will be apparent to those skilled in the art that changes and modifications may be made therein without departing from the spirit of the invention, the scope of which is defined by the appended claims.

What is claimed is:

1. An over the wire scalpel for making a skin nick in a patient's skin comprising:

a) a blade having a pair of cutting edges, said cutting edges meeting to define a tip;

b) a handle connected to said blade;

c) a blocker positioned behind the blade on said handle, said blocker dimensioned to limit travel of said blade into the patient's skin; and d) said blade and said handle having a central lumen passing therethrough with a leading opening positioned through the tip of the blade adapted to receive a guidewire for travel thereon to a desired location for the skin nick.

2. The over the wire scalpel of claim 1 further including a stylus which may be disposed within said central lumen, said stylus having a pointed end that protrudes from the tip of the blade, whereby the scalpel may be used without a guidewire.

3. The over the wire scalpel of claim 1 further including a stylus which may be disposed within said central lumen, said stylus having a lumen therethrough, whereby the scalpel may be used with smaller diameter guidewires.

4. The over the wire scalpel of claim 1 wherein said blade has a cross section that, along an end adjacent to the handle, is thickest in a region proximate to said central lumen, said cross section tapering in a direction away from the handle so as to ultimately define the pair of cutting edges and said tip.

5. The over the wire scalpel of claim 4 wherein the blade has a cross section that is generally diamond shaped along the end adjacent to the handle.

* * * * *